United States Patent [19]
Glass

[11] Patent Number: 5,698,083
[45] Date of Patent: Dec. 16, 1997

[54] CHEMIRESISTOR UREA SENSOR

[75] Inventor: Robert S. Glass, Livermore, Calif.

[73] Assignee: Regents of the University of California, Oakland, Calif.

[21] Appl. No.: 517,011

[22] Filed: Aug. 18, 1995

[51] Int. Cl.⁶ ............................................ G01N 27/26
[52] U.S. Cl. ..................... 204/403; 204/406; 204/415; 422/82.01; 422/82.02; 435/287.1; 435/289.1; 436/108; 436/114; 436/149; 436/150
[58] Field of Search .............................. 204/403, 406, 204/415, 416, 418; 422/68.1, 82.02, 82.01, 98; 435/4, 12, 288, 291; 128/637; 436/108, 114, 149, 151

[56] References Cited

U.S. PATENT DOCUMENTS

| | | | |
|---|---|---|---|
| 4,225,410 | 9/1980 | Place | 204/195 R |
| 4,244,787 | 1/1981 | Klein et al. | 204/1 T |
| 4,452,682 | 6/1984 | Takata et al. | 204/403 |
| 4,713,165 | 12/1987 | Conover et al. | 204/403 |
| 5,001,048 | 3/1991 | Taylor et al. | 436/151 |
| 5,053,225 | 10/1991 | Miyasaka et al. | 424/85.8 |
| 5,071,770 | 12/1991 | Kolesar, Jr. | 436/149 |
| 5,120,421 | 6/1992 | Glass et al. | 204/406 |
| 5,264,103 | 11/1993 | Yoshioka et al. | 204/403 |
| 5,308,315 | 5/1994 | Khuri et al. | 604/4 |
| 5,312,762 | 5/1994 | Guiseppi-Elie | 436/149 |
| 5,501,836 | 3/1996 | Myerson | 422/82.05 |

FOREIGN PATENT DOCUMENTS

| | | |
|---|---|---|
| 0 504 722 A2 | 9/1992 | European Pat. Off. . |
| 2 204 408 | 11/1988 | United Kingdom . |
| WO94/08641 | 4/1994 | WIPO . |

*Primary Examiner*—Bruce F. Bell
*Attorney, Agent, or Firm*—L. E. Carnahan; Henry P. Sartorio

[57] ABSTRACT

A sensor to detect and quantify urea in fluids resulting from hemodialysis procedures, and in blood and other body fluids. The sensor is based upon a chemiresistor, which consists of an interdigitated array of metal fingers between which a resistance measured. The interdigitated array is fabricated on a suitable substrate. The surface of the array of fingers is covered with a coating containing the enzyme urease which catalyzes the hydrolysis of urea to form the ammonium ion, the bicarbonate ion, and hydroxide-chemical products which provide the basis for the measured signal. In a typical application, the sensor could be used at bedside, in conjunction with an appropriate electronics/computer system, in order to determine the hemodialysis endpoint. Also, the chemiresistor used to detect urea, can be utilized with a reference chemiresistor which does not contain urease, and connected in a differential measurement arrangement, such that the reference chemiresistor would cancel out any fluctuations due to background effects.

10 Claims, 6 Drawing Sheets

CHEMIRESISTOR UREA SENSOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to electrochemical sensors, particularly such sensors for detecting urea in body fluids, and more particularly to a chemiresistor sensor capable of detecting and quantifying urea in fluids resulting from hemodialysis procedures, and in blood and other body fluids.

There are currently more than 300,000 people with end-stage renal disease in the United States who require regular hemodialysis. Urea is generally accepted to be the best marker for evaluating the level of uremic toxins. Dialysis procedures are therefore aimed at reduction of urea in the blood stream. Currently, most dialysis clinics use the simple index of time of dialysis to determine the adequacy of dialysis. Blood draws (or other methods of obtaining blood samples) to accurately measure the level of urea in blood can be done infrequently. The frequency of this measurement, which requires the use of clinical laboratories, varies from facility to facility. Turnaround times for these samples can be quite long, and often the patient must be recalled for further dialysis if the percentage reduction of urea in the blood is not sufficient. In the absence of a blood check, the use of time as a measure of completion, especially if hemodialysis is not carried out long enough, can clearly lead to morbidity and mortality. It has long been desired to have a sensor which could monitor the progress of the dialysis procedure in "real-time", thereby assuring that the procedure was complete and obviating the need for using clinical laboratories and the necessity for patient recall. The most convenient fluid to monitor is the dialysate, which is the capturing medium for blood contaminants during the hemodialysis process. Monitoring in dialysate would result in a completely in vitro procedure. By use of an appropriate sensor arrangement, the dialysate could be continuously or intermittently monitored at the point-of-care.

A further enhancement of this general principle is a home monitor, which would allow at-home testing to determine if dialysis was necessary. Such a home monitor is similar, in principle, to devices used for blood glucose testing by diabetics. This device would require a blood droplet sample by using a finger prick.

There has been substantial efforts in the prior art to provide a sensor which would satisfy the above-mentioned needs, and various electrochemical sensors for detecting urea in body fluids have been proposed. The prior efforts have centered primarily on the use of potentiometric devices, specifically, the common pH, ammonium, or ammonia gas sensing electrodes. These potentiometric sensors are exemplified by P. G. Pietta et al, Ann. N.Y. Acad. Sci., 672, 257–263 (1992); G. H. Hsiue et al, Polym. Mater. Sci. Eng., 57, 825–829 (1987); G. G. Guilbault et al, J. Amer. Chem. Soc., 92, 2533–2538 (1970); and D. S. Papastathpoulos et al, Anal. Chim. Acta, 79, 17 (1975). Only one recent effort has apparently been directed at creating a biosensor for urea by depositing a coating containing the enzyme urease over the interdigitated conductive members, as exemplified by United Kingdom Patent Application No. 2204 408 A published Nov. 9, 1988.

Other publications teach of the need for dialysis or blood urea monitoring, and various mechanical systems which could be used in such a system, albeit with different or unspecified urea detection (sensor) methods than those of the present invention (see, for example, International Patent WO94/08641, April 1994, to P. Keshaviah et al; European Patent EP504772, November 1992 to B. Skerratt; and U.S. Pat. No. 4,452,682 issued June 1984 to Y. N. Takata et al; U.S. Pat. No. 3,930,957 issued January 1976 to J. P. Cummings et al; U.S. Pat. No. 4,225,410 issued September 1980 to S. J. Pace; U.S. Pat. No. 5,308,315 issued May 1994 to R. N. Khuri et al; U.S. Pat. No. 4,244,787 issued January 1981 to E. Klein et al. The prior approaches also describe various methods of enzyme (urease) immobilization to various substrates and for detection of urea in blood or in dialysate fluid. Other urease encapsulation techniques are described in other literature, as exemplified by U.S. Pat. No. 5,053,225 issued October 1991 to T. Miyasaka et al, and U.S. Pat. No. 4,713,165 issued December 1987 to G. Conover et al. None of the above previous approaches describe a combination of chemiresistors, ease of sol-gel encapsulation, mass fabricated sensors with disposability features, hemodialysis and home capillary blood monitoring, and electronics necessary for signal transduction. Previous efforts have also emphasized the need for high input impedance electronic measuring equipment which may distort the response.

These prior known sensors have not enabled the desired monitoring of the progress of the hemodialysis procedure in "real-time", thereby assuring that the procedure was complete, although the United Kingdom Application cited above provides an instrument having application in the analysis of urea for in vitro blood analysis and in dialysis monitoring. The sensor of this invention satisfies this long felt need and enables the continuous or intermediate monitoring in vitro and at bedside. The sensor of this invention could be used with an appropriate electronics package to provide detection and quantification of urea in body fluids, as well as being combined with a computerized system which would contain individual patient case histories, to determine the hemodialysis end points.

SUMMARY OF THE INVENTION

It is an object of the present invention to provide a chemiresistor sensor capable of detecting and quantifying desired components in body fluids.

A further object of the invention is to provide a chemiresistor urea sensor, and method of making same.

A further object of the invention is to provide a urea sensor and associated system for continuous or intermediate monitoring of urea in vitro and at bedside to determine hemodialysis end points.

Another object of the invention is to provide a sensor to detect and quantify urea in fluids resulting from hemodialysis procedures, and in blood and other body fluids.

Another object of the invention is to provide a urea sensor based upon a chemiresistor which utilizes an interdigitated array of metal fingers between which a resistance is measured, and which is covered with a coating containing the enzyme urease which catalyzes the hydrolysis of urea to form a chemical product which provides the basis for a measured signal.

Another object of the invention is to provide a sensor capable of use at bedside and in conjunction with an appropriate electronics/computer system in order to determine the hemodialysis endpoint.

Other objects and advantages will become apparent from the following description and accompanying drawings. Basically the invention is a sensor to detect and quantify urea in fluids resulting from hemodialysis procedures, and in blood and other body fluids. The sensor of this invention is based upon a chemiresistor which includes an interdigitated array of metal fingers between which a resistance is measured. The interdigitated array is fabricated on a suitable substrate, and the surface of the device is covered with a coating containing the enzyme urease which catalyzes the hydrolysis of urea to form ammonia and carbon dioxide (which, when dissolved in water form the ammonium, bicarbonate, and hydroxide ions), which provide the basis for the measured signal. An embodiment of the sensor utilizes at least fifty "pairs" of interdigitated fingers, with each finger of each pair being electrically connected to a common contact strip. By way of example, the fingers of each pair of interdigitated fingers have a width of 10–15 μm, a length of 200 μm to 4.8 mm and are separated by a distance of 10–15 μm, and are fabricated, for example, by sputter deposition and photolithography on an insulated substrate, such as a silicon (Si) wafer with a coating of $SiO_2$. The fingers, for example, may be composed of a thin (1000–2000 Å) layer of metal, such as gold or platinum, and to improve adhesion to the substrate, an underlying layer of adhesive material, such as titanium, may be utilized. The fingers are then covered with a coating containing the enzyme urease.

BRIEF DESCRIPTION OF THE DRAWINGS

The accompanying drawing, which are incorporated into and form a part of the disclosure, illustrate an embodiments of the invention, and an electronics/computer system therefore and, together with the description, serve to explain the principles of the invention.

DETAILED DESCRIPTION OF THE INVENTION

Figure 1:
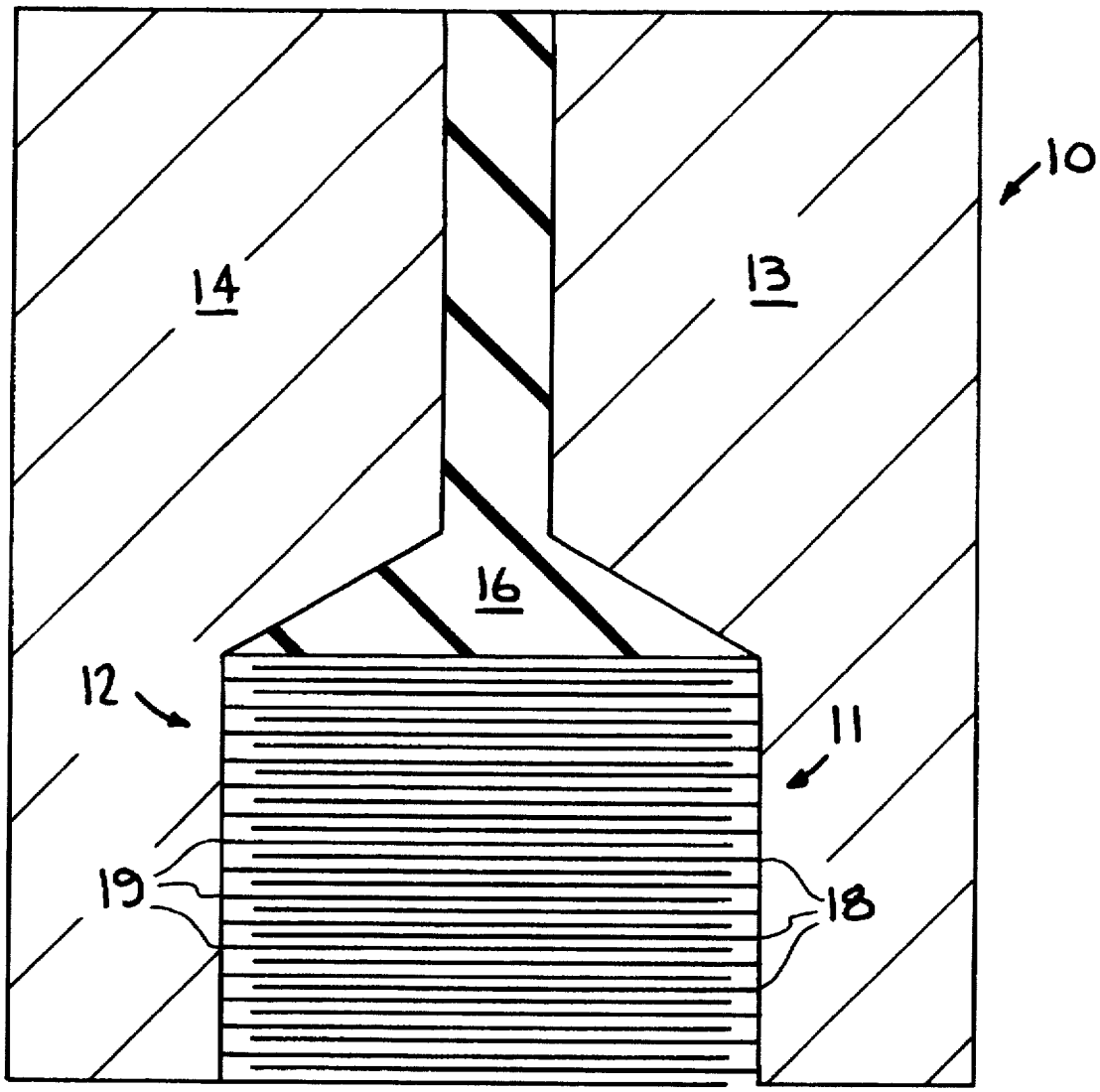
FIG. 1 illustrates an embodiment of a chemiresistor sensor containing one set of interdigitated fingers made in accordance with the present inventor.

The present invention is directed to a chemiresistor sensor, particularly adapted for detecting and quantifying urea in fluids resulting from hemodialysis procedures, and in blood and other body fluids. The chemiresistor utilizes an interdigitated array of metal fingers on a suitable substrate and between which a resistance is measured, with the surface of at least the array of fingers being covered with a coating containing the enzyme urease which catalyzes the hydrolysis of urea to form ammonia or carbon dioxide, chemical products which provide the basis for a measured signal. The sensor can be utilized alone or in combination with a reference sensor, and with an appropriate electronics/ computer system in order to determine the hemodialysis endpoint.

Prior to a detailed description of the embodiments illustrated in the drawings and the process for producing the sensor, the following general information is provided.

The chemiresistor sensor consists of two sets of interdigitated fingers deposited on an insulated substrate, with each set having 50–200 fingers, and each set of fingers is connected to a common contact strip or conductor bar. For either gas or liquid phase sensing, the resistance between the two sets of fingers is monitored. Typically, a coating is applied to the surface of the sensor which contains a component which reacts specifically with the gas or liquid phase species to be detected. For a urea sensor, the coating contains urease. Urease can either be physically entrapped or covalently bound within the coating. The coating will typically be a polymer, such as poly (vinyl alcohol), and copolymers of poly (vinyl alcohol), polypyrrole, polyvinylpyridine, polyalkylthiophenes, etc., or contain something like Ab-antiurease, to which urease can be covalently attached. Also, the coating can be a urea impregnated sol-gel. The analysis procedure relies upon the enzyme-catalyzed hydrolysis of urea, which in aqueous solution yields ammonium, bicarbonate and hydroxide ions:

$$Urea+H_2O=>2NH_4^+ +HCO_3^- +OH^-$$

Formed within the coating, the reaction products will influence the resistance measured between the two sets of fingers. The response will be proportional to the concentration of urea in the fluid being monitored. Alternatively, the coating may be in part composed of certain agents which have intrinsic conductivity properties, such as the conductive polymers, or monomeric species, which may complex with the reaction products, thereby producing a change in the resistance of the coating which can be measured.

In addition to the chemiresistor which is used to detect urea, a reference chemiresistor without urease in the coating can be utilized therewith in a differential measurement arrangement, such as described hereinafter with respect to FIG. 11. The reference chemiresistor would cancel out all background interferences which could cause resistance changes within the coating.

The sensing elements can also be used with an instrumentation package capable of measuring resistance by ac techniques, as in commonly known from the prior art. Any convenient computer can be interfaced to automate data collection, storage, analysis, and display. Such as instrumentation package is described with respect to FIG. 13. The computer would be supplied with the appropriate patient-specific profiles in order to better determine effective hemodialysis end-points.

The advantages of the chemiresistor compared to previous approaches to construct urea sensors include a faster response, a more accurate specific response to urea than alternative solution-based conductivity measurements and greater sensitivity in the analytical region of interest. Previous electrochemical sensors based upon pH, ammonium, or ammonia gas electrodes all respond logarithmically. Therefore, a device having a linear response to urea (which may be possible with a chemiresistor), would provide greater accuracy in the end-point determinations for dialysis. Also, the solid state chemiresistors would be more durable than some potentiometric electrodes, which use aqueous systems encased within fragile glass tubes. In addition, because of the mass fabrication capability, the chemiresistors would be inexpensive enough so that they could be disposed of following some prescribed period of use.

Figure 2:
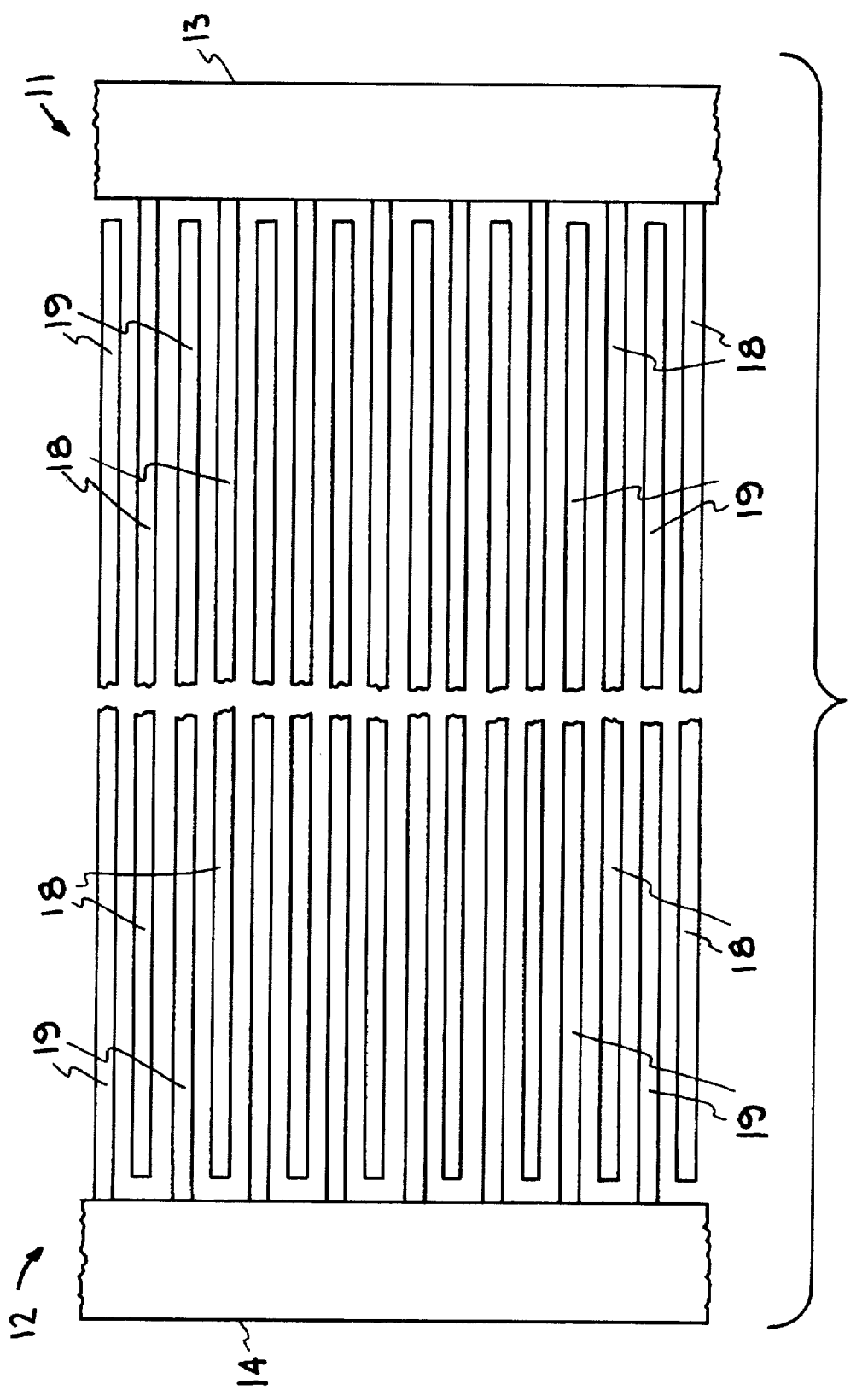
FIG. 2 is a greatly enlarged partial section of the interdigitated pairs of fingers of the FIG. 1 sensor, with ends of the alternating fingers being connected to a pair of common side strip conductors.
Figure 3:
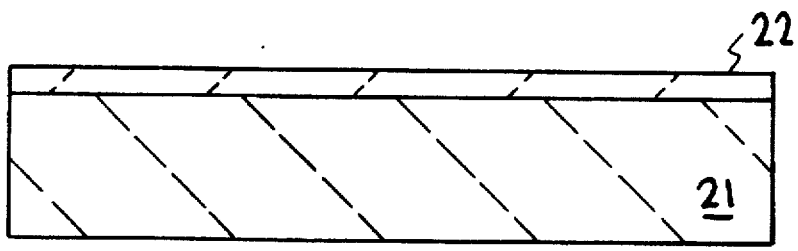
FIGS. 3–9 illustrate a process for fabricating the interdigitated pairs of fingers on a substrate.
Figure 4:
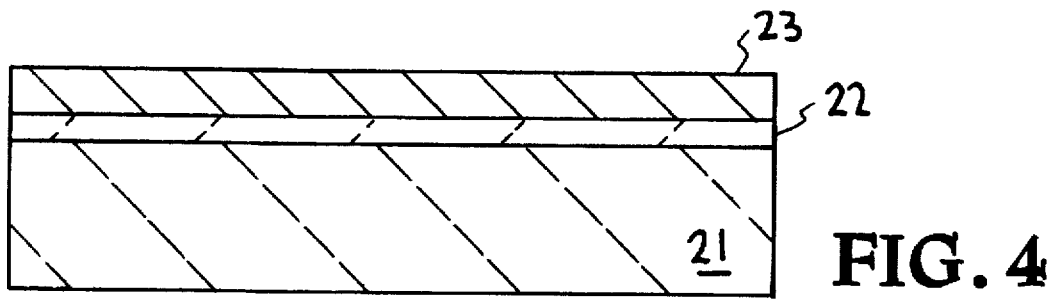
Figure 5:
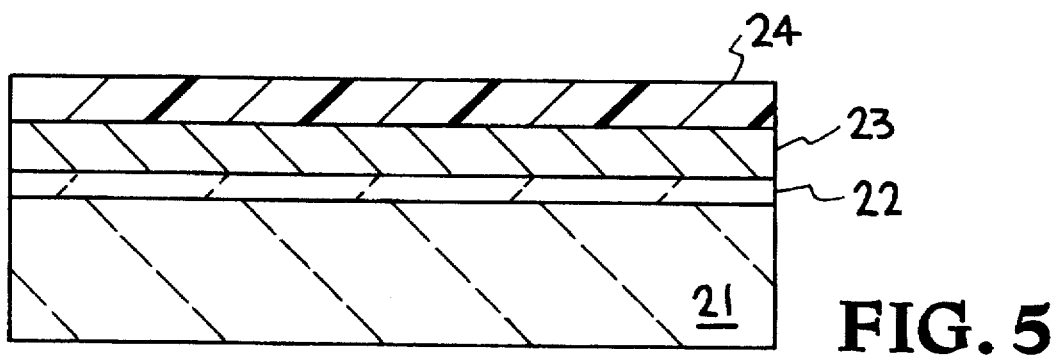
Figure 6:
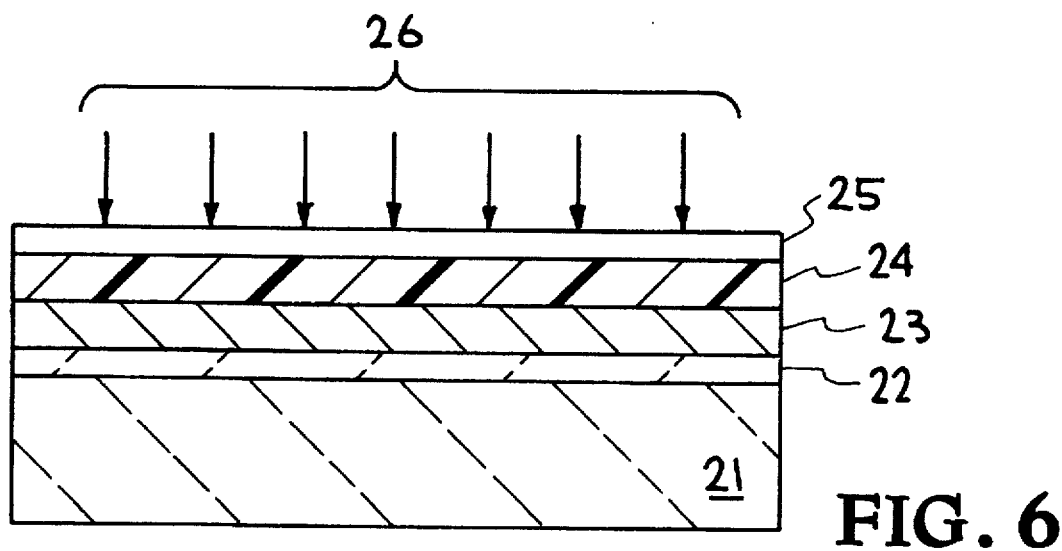
Figure 7:
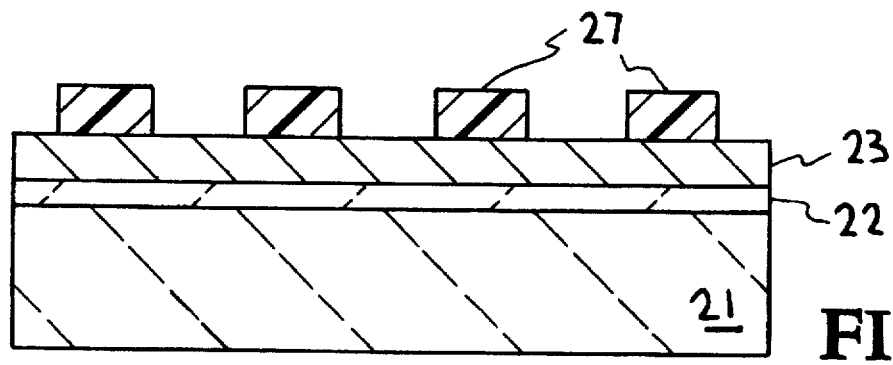
Figure 8:
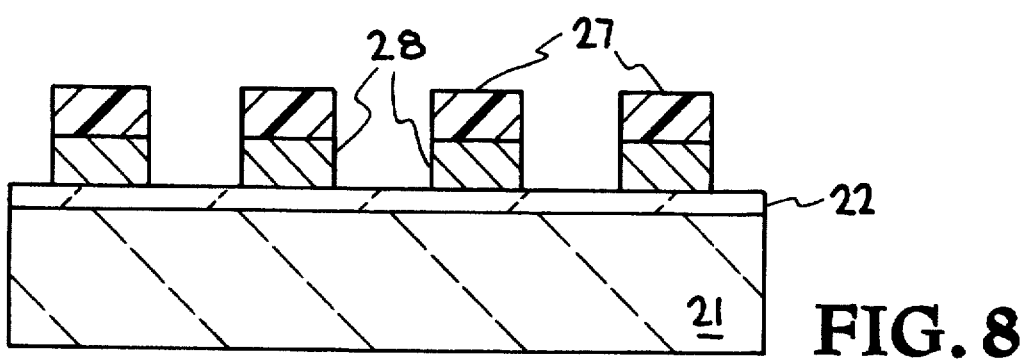
Figure 9:
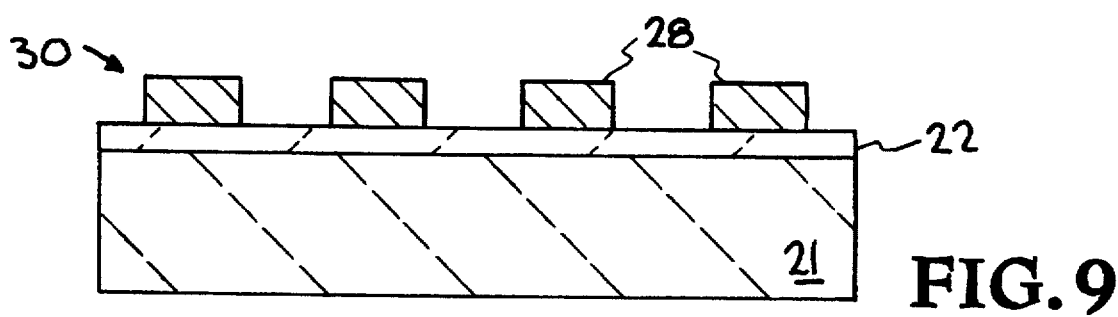
Figure 10:
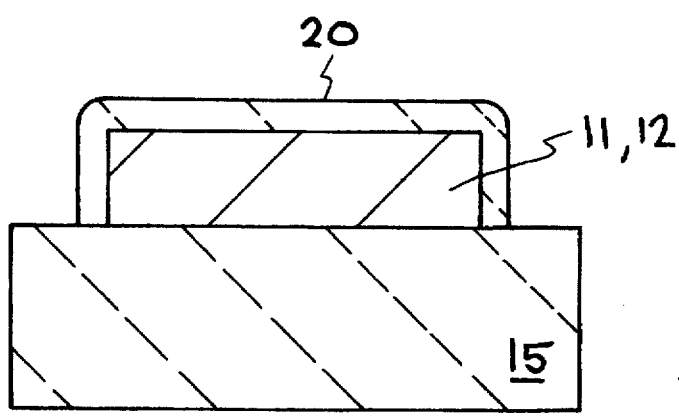
FIG. 10 is a cross-sectional view of a urea sensor of this invention, illustrating the insulated substrate on which the fingers are deposited, such as made by the process of FIGS. 3–9, and the urease containing coating covering the fingers.

Referring now to the illustrated embodiments and the fabrication process, FIGS. 1, 2, and 10 illustrate a first embodiment of a chemiresistor, generally indicated at 10 and which consists of two sets of interdigitated fingers, generally indicated at 11 and 12, each set being connected to an electrical conductor or contact pads 13 and 14. The sets of fingers are deposited on an insulated substrate 15 (see FIG. 10), which for example may be a 1 mm thick silicon (Si) wafer covered with a 1 µm thick coating of silicon dioxide ($SiO_2$). Conventional methods of sputter deposition and photolithography are used for sensor fabrication, as described hereinafter with respect to FIGS. 3–9. The two sets of interdigitated fingers 11 and 12, as shown greatly enlarged in FIG. 2, each comprise a common conductor, side strip, or contact pads 13 and 14 from which fingers or conductive members 18 and 19, respectively, extend. The fingers and side strips or contact pads may be constructed of gold, platinum, iridium, carbon, and several other metals or other electrically conductive materials which are inert (i.e., essentially do not corrode) in the dialysate medium, or in other test buffers, and upon which the coatings containing urease remain adherent. By way of example, in FIGS. 1 and 2 the fingers 18–19 and side strips 13–14 are gold with a thickness of 2000 Å deposited on the silicon substrate 15, with a thin (100 Å) adhesive layer, not shown, of titanium, for example, therebetween. The fingers or conductive members 18–19, for example are 10–15 µm wide, by approximately 4.8 mm long, and separated by 10–15 µm, with a space of 10–15 µm between the ends of the fingers 18 or 19 and the opposite side strip 14 or 13, as seen in FIG. 2. The side strips 13 and 14 have a width of 300 µm. The side strips 13 and 14 are electrically insulated from each other by an insulator 16, as seen in FIG. 1. As shown in FIG. 10, the sets of interdigitated fingers 11 and 12 are covered with a coating 20 having a thickness of 0.1 to 10 µm, with a typical thickness of 1–3 µm, and containing a desired component, such as the enzyme urease, as described in greater detail hereinafter.

As seen in FIGS. 1, 2, and 10, the chemiresistor sensor basically consisting of an interdigitated array of conductive (gold) fingers on an insulating substrate (silicon/silicon dioxide) and covered by a coating containing a desired reactive material, such as the enzyme urease. It is important that the materials used for sensor construction be inert in the media in which they are used. That is, they must not corrode or in any other fashion react chemically. The fingers and substrate serve basically as the electrical contact and support pattern for any overlying layer containing reactive components, such as the enzyme urease.

The following sets forth a process, with reference to FIGS. 3–9, for producing the chemiresistor without the coating:

1. A substrate 21 (indicated at 15 in FIG. 10) such as a standard 2–3 inch diameter silicon wafer (100 orientation), having a thickness of 12 mils is cleaned by conventional techniques. The substrate 21 could also be composed of aluminum oxide, KAPTON (Polyimide), or other non-conductive ceramic or polymeric material compatible with subsequent processing steps.

2. In order to create a highly insulating substrate, a layer 22 at least 1000–2000 Å thick of silicon nitride or silicon dioxide is deposited on the silicon wafer 21 (see FIG. 3) using low pressure chemical vapor deposition for the silicon nitride or thermal oxidation for the silicon oxide.

3. Where gold, for example, is utilized as the conductive metal for the fingers, an adhesion layer, not shown, typically 100 Å of chromium or titanium, is deposited on the insulating layer 22 to ensure adhesion of the metal fingers.

4. A metallic layer 23, such as gold, having a thickness of 0.5 µm is deposited on the adhesive layer or on insulating layer 22 (see FIG. 4), by electron beam evaporation or dc magnetron sputtering.

5. A layer 24 of photoresist is formed on top of the metallic layer 23 (see FIG. 5). For example, the layer 24 may be of positive photoresist, such as AZ1350J supplied by Hoechst Celanese Corporation. Typically, the photoresist is spun onto the metallic layer 23 at 4000 rpm, which takes about 25 seconds to deposit a layer 1.25 µm in thickness. The photoresist layer 24 is then allowed to soft bake at 90° C. for 25 minutes, and then allowed to cool.

6. A desired metal conductor pattern for the two sets of fingers and side conductors, such as shown in FIG. 2, is then established by UV irradiation of the photoresist layer 24 through a suitable photomask 25 (see FIG. 6). The photomask is designed using a computer-aided design (CAD) system, and a irradiation source/mask aligner is used to print the image onto the photoresist layer 24. The irradiation source/mask aligner uses a 405 nm ultraviolet (UV) source with an intensity of 10 mW/cm$^2$. About 140 mJ/cm$^2$ is used to properly expose the photoresist, and this energy is generally indicated by arrows 26. The photoresist is then developed in a 1:1 mixture of AZ Developer, made by Hoechst Celanese Corporation, and water. It takes 30 seconds to develop away the UV exposed areas of the photoresist resulting in a pattern of unexposed photoresist indicated at 27 in FIG. 7. The assembly is then blown dry in nitrogen and hard baked at 120° C. for 20 minutes.

7. The exposed metallic conducting pattern is then etched chemically to remove traces of photoresist and other surface contaminants, using the remaining photoresist as an etch pattern. This produces a pattern of metallic conductor material overlaid with photoresist. If gold is used as the metallic conductor layer 23, potassium iodide is used as the etchant. The etch time for 0.5 micron of gold is typically about one minute.

8. The exposed adhesive layer of chromium or titanium is then etched; a chromium adhesion layer is etched in a chromium etchant for about 15 seconds.

9. Following the etching of metallic conductor layer and adhesive layer etch, the remaining photoresist 27 is stripped off in acetone (see FIG. 9) and the assembly is plasma cleaned in an oxygen plasma for 10 minutes at a power level of 300 Watts, resulting in the end product of chemiresistor indicated at 30, as illustrated in FIG. 9, wherein the metallic components 28 constitute the sets of interdigitated fingers 11 and 12 of FIGS. 1, 2, and 10.

The bare (uncoated) chemiresistor 30 of FIG. 9 is then overlaid with an overlay or coating containing a bioactive components, such as the enzyme urease which catalyzes the hydrolysis of urea, as indicated 20 in FIG. 10, or with an overlay or coating containing no bioactive component, thus being a modifying or protective layer only. The overlaying layer or coating 20 may be attached to the sets of fingers through covalent chemical interactions or through physical adsorption. Gel-like coatings may also be used.

Thus, the above-described process of FIGS. 3–9 results in the formation of a bare chemiresistor 30 (see FIG. 9) which is then coated with a reactive layer to form the chemiresistor sensor of FIG. 10. The above process enables the fabrication of the chemiresistor sensor and the reference chemiresistor described hereinafter with respect to FIG. 11.

Figure 13:
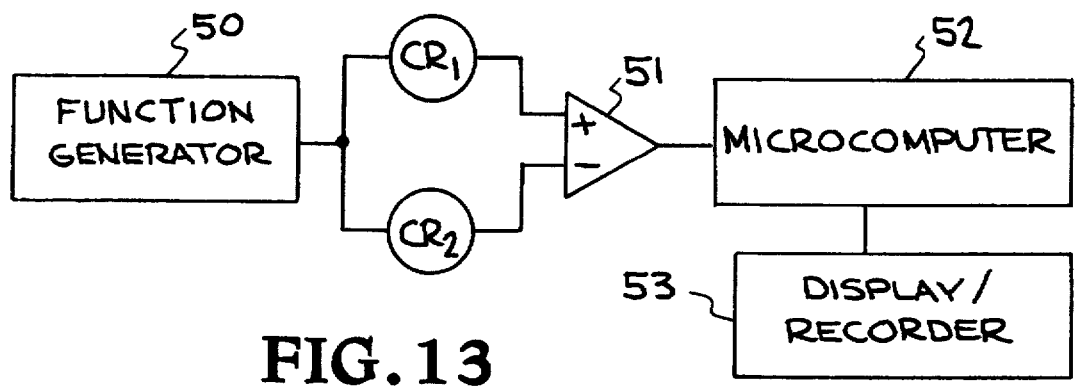
FIG. 13 schematically illustrates a chemiresistor urea sensor, made in accordance with the present invention, mounted in conjunction with a reference chemiresistor and an appropriate electronics/computer system, in order to determine the hemodialysis endpoint.

The chemiresistor sensor of FIGS. 1, 2, and 10, contains only a single set of interdigitated fingers. With this sensor, no "background" correction is possible. That is, the sensor will respond not only to the presence of urea, as described above, but also any changes in ionic strength in the dialysate medium which could also produce changes in conductivity within the coating. For instance, the concentration of chloride, borate, phosphate or other ion may vary. Temperature changes could also affect conductivity measurements. In such unlikely cases in which these "background" changes may occur, a reference chemiresistor may be used along with the urea measuring chemiresistor. Such an approach is illustrated in FIG. 11, which includes a chemiresistor sensor indicated at $CR_1$, which contains urease, for example, and a reference chemiresistor $CR_2$, which contains no urease. The interdigitated fingers 11' and 12' of chemiresistor sensor $CR_1$ are connected to contact pads 31 and 32, while the interdigitated fingers 11' and 12' of reference chemiresistor $CR_2$ are connected to contact pads 33 and 34. The contact pads 31–32 and 33–34 are adapted to be connected to a differential measurement electronic instrument, such as illustrated in FIG. 13. In the FIG. 11 embodiment, each of the units $CR_1$ and $CR_2$ contain an array of interdigitated fingers similar to FIG. 2, containing 340 lines or 170 pairs of fingers, with each finger being 10 µm wide, 4.8 mm long, separated from an adjacent finger by 10 µm, with a space between the end of the fingers and the opposite side strip or conductor being 10 µm.

Figure 11:
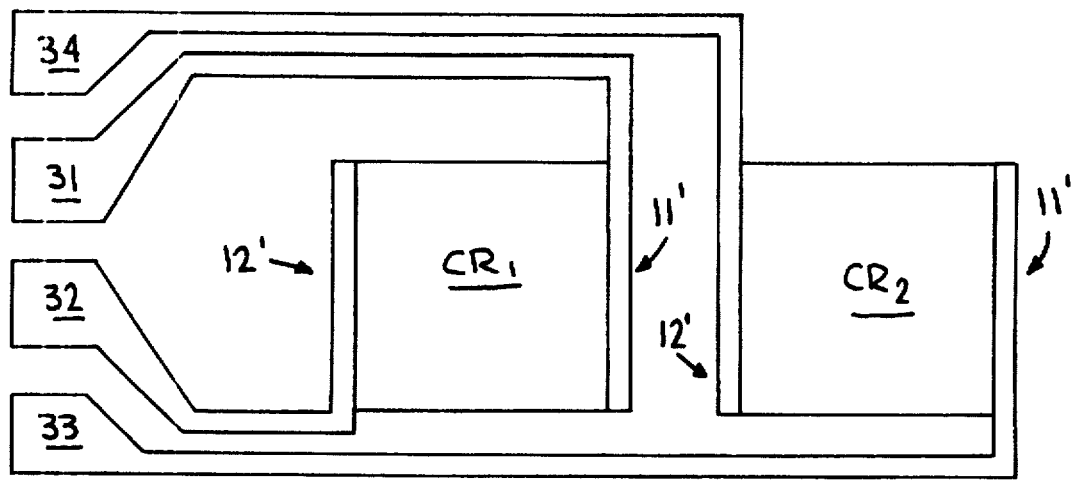
FIG. 11 schematically illustrates a chemiresistor, such as illustrated in FIGS. 2 and 10, and a chemiresistor, similar to that of FIG. 2, without the urease within the coating which acts as a reference chemiresistor to eliminate background interferences which cause resistance changes within the urease containing coating.

In FIG. 11, the reference chemiresistor $CR_2$ has the same base metal finger design of the urea sensing chemiresistor $CR_1$. However, a coating applied to the interdigitated set of fingers in $CR_2$ does not contain the enzyme urease. The reference chemiresistor $CR_2$ will therefore respond only to conductivity changes resulting from variation in the concentrations of all ions present in the dialysate medium, or other physical variables like temperature; urea will not contribute. Placing the reference chemiresistor $CR_2$ on the same chip or substrate as the chemiresistor sensor $CR_1$ is a convenient method for performing background subtraction. The analytically useful signal, which is used to correlate the response of the sensor to the concentration of urea is therefore:

[Urea]∝Response $CR_1$—Response $CR_2$

The result of this measurement, which would be performed before and after dialysis, would be used to compute the percent reduction of urea in the dialysate as a measure of the effectiveness of hemodialysis. The relevant numerical result would be:

$$\text{Percent (\%) urea reduction} = \frac{[R_{CR_1} - R_{CR_2}]_t}{[R_{CR_1} - R_{CR_2}]_0} \times 100,$$

where R is the response of the urea sensor or reference chemiresistor, t is the measurement at time t after the start of dialysis, and subscript "0" indicates the results at the start of dialysis. It is to be noted that other quantitative expressions for the efficiency of dialysis have been proposed (see, for example, above-referenced U.S. Pat. No. 5,308,315), which may also be used with the sensor of this invention.

There are a variety of mechanisms by which the enzyme urease, for example, may be immobilized in a coating or layer covering the interdigitated fingers of the array, as shown in FIG. 10. These include covalent attachment through a monomeric chemical bridge; covalent attachment within an electroactive polymer; physical entrapment within an electroactive polymer as it is polymerized onto the electrodes (fingers); physical entrapment within some other polymer or hydrogel which can be applied using a number of standard methods (e.g., dipping, spraying, painting, etc.); and incorporation within sol-gel layers. Sol-gel polycondensation is particularly appealing as a method of incorporating the urease. Generally, the sol-gel processing method involves the hydrolysis and condensation of metal alkoxides to form inorganic xerogels or aerogels. For instance, a one or two-step catalyzed procedure can be used to polymerize a silica xerogel beginning with the monomer tetramethoxysilane. Similarly, organic xerogels can be made from the aqueous polycondensation of resorcinol with formaldehyde. These processes result in transparent materials. The processing techniques of silica and organic sol-gel materials are well known. See for example, *Better Ceramics Through Chemistry* V1, A. K. Cheetham et al., Eds., Vol. 346, Materials Research Society, Pittsburgh, Pa. (1994).

Research has shown that it is possible to tailor the properties of sol-gels. These materials have been produced with ultra fine cell/pore sizes (less than 100 nm) and very high surface areas (400–1000 m²/g). They are monolithic solids, internally connected by colloidal-like particles or polymeric chains having diameters on the order of 10 nm. It is the unique nanostructure which is responsible for the unusual optical, thermal, electrical, and other properties of these materials. For a urea sensor, the enzyme urease would be incorporated within the sol-gel coating deposited onto the chemiresistor surface. As the sol-gel begins to dry, and continues to crosslink, the urease would become increasingly immobilized. A thin layer would be used for optimal response time. Some of the advantages of sol-gel urea biosensors include: simplicity of fabrication; maintenance of activity of the encapsulated enzyme/bioactive component; prevention of loss of enzyme, dyes, or other large molecules from the coating by diffusion; maintenance of an aqueous environment within the membrane, which is necessary for enzyme function; transparency; and filtering capacity.

Figure 12:
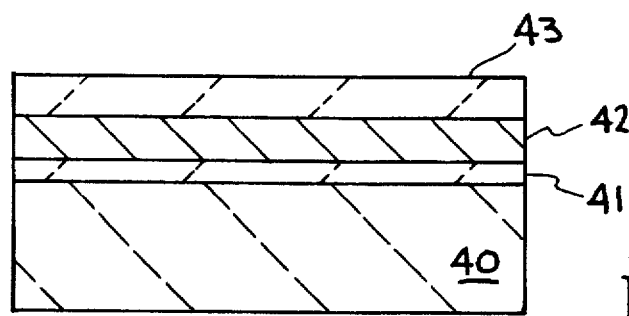
FIG. 12 illustrates in cross-section another embodiment of a chemiresistor, wherein the enzyme urease is immobilized in a layer of sol-gel covering the interdigitated pairs of fingers, such as shown in FIG. 2.

A schematic of sol-gel based urea chemiresistor is shown in FIG. 12, which comprises a silicon substrate 40, a coating or oxide layer 41 of silicon nitride, silicon dioxide, etc. a layer containing at least one set of patterned interdigitated conductive fingers indicated at 42, and a sol-gel coating 43 (1–3 µm) containing a bioactive material, such as urease, or without the bioactive material to form a reference chemiresistor. The substrate 40 and the layers 41 and 42 may be fabricated as described above with respect to the FIG. 10 embodiment, and may include an adhesive layer intermediate the silicon substrate and the metallic finger pattern, if needed.

A particularly effective sol-gel coating method for biosensors can be found in the literature, for instance for glucose (U. Narang, et al, Anal Chem. 66:3139–3144 (1994)). One takes an appropriate substrate (in our case, the chemiresistor) and spin coats onto this substrate a three layer sol-gel coating. The coating solutions and order of coating is: stock sol-gel solution, followed by enzyme containing solution, followed by diluted stock sol-gel solution. For instance, a useful stock solution (for a silica sol-gel) would be made from 4.5 ml of tetraethyl orthosilicate, 1.4 ml $H_2O$ and 100 µl of 0.1M HCl. The diluted form of this would be produced by taking 0.5 ml of the stock and adding 2.0 ml of water. A typical enzyme coating solution would consist of an aqueous solution (with or without phosphate or other buffer) containing approximately 5000 I.U./ml of the enzyme (for example, urease). Coating is done with a spin coater at 3000 rpm for 30s for each layer. This procedure could generate a coating less than 2.0 µm in thickness.

To measure response, alternating current (ac) conductivity measurements (typically sinusoidal, althrough some other appropriate time-varying signal, such as triangular or square waves may also be used) are preferred because they minimize perturbation of the interfaces (avoid faradaic reaction, double layer charging, concentration polarization effects, effects known to those skilled in the art). In this method, by way of example, a small sinusoidal voltage signal in the kHz range with 10 mV peak-to-peak is applied and the cell impedance is measured. FIG. 13 shows in block diagram form, the essential components for obtaining measurements from the chemiresistor array. The arrangement of FIG. 13 pertains to the use of a urea sensor array in conjunction with a reference array, as illustrated in FIG. 11.

In FIG. 13, a function generator, indicated at 50, supplies an appropriate small amplitude time-varying signal (e.g., sine wave, triangular wave, or square wave) to a monitoring chemiresistor sensor, $CR_1$, and reference chemiresistor, $CR_2$. The monitoring chemiresistor sensor $CR_1$ contains the enzyme urease entrained in the coating. The reference chemiresistor sensor $CR_2$ contains all the other components in the coating, except for urease. The outputs of $CR_1$ and $CR_2$ are inputted into a differential amplifier, indicated at 51. The output of the differential amplifier 51 is inputted into a microcomputer, indicated at 52. The microcomputer 52 provides an output signal, related to the urea concentration in the sample, which is output to a display or some other form of recorder, indicated at 53. The arrangement of FIG. 13 represents a completely automated form of data acquisition and display. That is, the function generator can be made to initiate a one time and "instantaneous" measurement by manually depressing an integrated button or switch of some sort, or it can continually cycle the chemiresistors $CR_1$ and $CR_2$ through measurement programs. If desired, the microcomputer 52 can be supplied with stored memory so that patient-specific information (e.g., typical values for percent reduction of urea during dialysis) can be displayed on the screen for treatment decision-making.

The design of the circuitry of the FIG. 13 embodiment, and potential miniaturization of the circuit components, can result in a device which can be fabricated "on a chip" through integrated circuit manufacturing techniques, resulting in, at least, a hand-held instrument.

While the major application for the chemiresistor sensor of this invention is for monitoring dialysis, other modes of operation are also possible. For example, the chemiresistor urea sensor could be employed as part of a urea monitor used at home, similar to that exemplified by the home glucose monitor. In this regard, urea in whole blood, obtained by "finger stick" methods, would be measured. Calibration would be done by test sensor "lot", similar to the glucose systems. A chemiresistor with known conductivity would be supplied with each container of test chemiresistors. It is better in this regard if the test structures were fabricated on a flexible substrate, such as KAPTON or reinforced composite or other plastic material. Depending upon test results, the patient could ascertain whether hemodialysis was necessary.

Figure 14A:
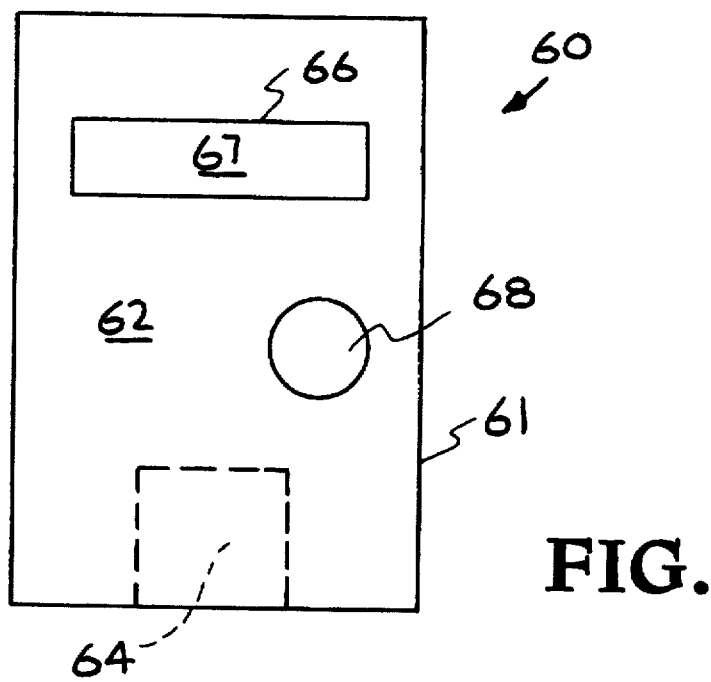
FIGS. 14A–14C illustrate an embodiment of a test device utilizing the invention.
Figure 14B:
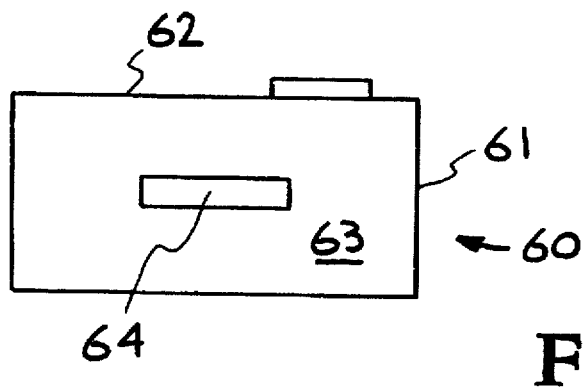
Figure 14C:
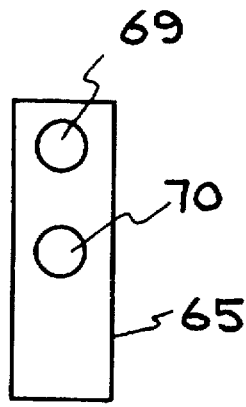

FIGS. 14A–14C illustrate a home monitor arrangement for the use of the urea sensor for capillary blood urea monitoring. The electronics necessary to make measurement is substantially the same as that depicted in FIG. 13, with only the $CR_2$ circuitry necessary, along with components 52 and 53 of FIG. 13, and microcomputer 52 could be replaced with a microprocessor chip. In addition, initiation of measurement cycles would be provided through a push button prior to application of a blood droplet to the test strip. In contrast to glucose monitors, it is expected that the urea monitor would be used semi-quantitatively as a gauge, indicating necessity for dialysis, and to schedule treatments, and not for blood urea control. Referring now to the particular embodiment of the "home urea" monitor, as illustrated in FIGS. 14A–14C, the embodiment comprises a meter, generally indicated at 60, having a housing or casing 61 (see FIG. 14B) with a face plate 62. An end 63 of housing 61 (see FIG. 14B) is provided with a slot 64 to insert a test strip 65 (see FIG. 14C). Face plate 62 is provided with an opening 66 beneath which is a readout 67 to provide a reading of the test strip 65. An off-on button or switch 68 is positioned on face plate 62. Test strip 65 (see FIG. 14C) includes an electrical contact or connection section or area 69 adapted to contact an electrical circuit within housing 61, and a sample area or section 70 onto which a blood drop is deposited after insertion of test strip 65 into slot 64 of housing 61. Electrical connectors (covered by inert material) run from the contact pads 69 to the test area 70. The sample area 70 essentially consists of the chemiresistor patterns displayed in FIGS. 1, 2, or 10. As for the in vitro dialysis sensor, these test strips would have a coating containing urease deposited on the interdigitated finger substrate. If a reference is used, the coating again would contain all of the same ingredients as the urea sensor except urease. Any convenient coating method can be used for the test strips, as discussed in reference to FIGS. 10 and 12. The substrate for the test strips can either be rigid (e.g., insulated silicon or ceramic) or somewhat flexible KAPTON or other plastic or reinforced material, but in any case must be sturdy enough to withstand the mechanical processes involved in insertion into the meter.

It has thus been shown that the invention provides an apparatus capable of quantifying urea in fluids resulting from hemodialysis procedures, and in blood and other body fluids. The sensor of this invention can be used at bedside, in conjunction with an appropriate electronics/computer system, in order to determine the hemodialysis end point. The sensor can be utilized with or without a similarly constructed reference chemiresistor, which can be fabricated by the same method. The sensor/monitor arrangement can be utilized where patients are undergoing hemodialysis treatment, and such would reduce the cost of dialysis treatment, and other procedures where there is a need to monitor urea; and would reduce exposure of medical staff to blood-borne disease, as well as reduce patient discomfort and enhance overall well-being.

While particular embodiments, fabrication method, materials, parameters, etc., as well as an overall sensor/ monitor arrangement have been illustrated and or described to exemplify the invention and its operating principles, such are not intended to be limiting. Modifications and changes may become apparent to those skilled in the art, and it is intended that the invention be limited only by the scope of the appended claims.

The invention claimed is:

1. A chemiresistor device in combination with a urea monitor, said chemiresistor device comprising:

a substrate, an insulating layer deposited on at least one surface of the substrate, at least a patterned layer of conductive material including at least one set of interdigitated members deposited on said insulating layer, and a layer of encapsulation material deposited on at least the interdigitated members, said layer of encapsulated material being composed of a sol-gel and including an immobilized bioactive component composed of urease, said urea monitor comprising, a housing having said chemiresistor device operatively mounted therein, and electronic means and readout means therefore, said housing being provided with means for inserting a test strip into said housing for providing a reading of urea conditions via said readout means.

2. The combination of claim 1, wherein said layer of conductive material includes a plurality of sets of interdigitated members, and wherein said layer of material encapsulation on at least one of said plurality of sets of interdigitated members includes the bioactive component urease.

3. The combination of claim 1, additionally including a layer of adhesive material under the layer of conductive material.

4. The combination of claim 1, wherein said substrate is composed of material selected from the group consisting of silicon, aluminum oxide, polyimide (KAPTON), ceramic materials, and polymeric materials.

5. The combination of claim 1, wherein said insulating layer is composed of material selected from the group consisting of silicon nitride and silicon dioxide.

6. The combination of claim 1, wherein said layer of conductive material is composed of material selected from the group consisting of gold, platinum, iridium, carbon, and conductive, inert materials.

7. The combination of claim 1, wherein said layer of conductive material has a thickness of 0.1 to 1.0 µm, wherein said interdigitated members have a width of 10–15 µm, a length of 200 µm to 4.8 mm, and are separated from one another by a distance of 10–15 µm.

8. The combination of claim 7, wherein said set of interdigitated members comprises a pair of opposing side strips and a plurality of members attached to each of said side strips, and wherein an end of the members attached to one side strip is spaced from an opposing side strip by a distance of 10–15 µm.

9. The combination of claim 1, wherein said test strip includes an electrical contact section and a sample section.

10. An apparatus for detecting/monitoring urea, including:

a chemiresistor sensor containing an array of interdigitated fingers covered by a coating composed of a sol-gel containing urease, a reference chemiresistor, containing an array of interdigitated fingers without a coating containing urease, said chemiresistor sensor and said reference chemiresistor being operatively connected to a differential amplifier, said differential amplifier being operatively connected to a microcomputer, a function generator operatively connected to at least one of said chemiresistor sensor and said reference chemiresistor, and a display/recorder mechanism operatively connected to said microcomputer.

* * * * *